United States Patent [19]

Werner et al.

[11] Patent Number: 4,636,565

[45] Date of Patent: Jan. 13, 1987

[54] PREPARATION OF 2,3-DICHLORO-5-TRICHLOROMETHYL-PYRIDINE

[75] Inventors: John A. Werner, Menlo Park; Charles A. Wilson, Pittsburg, both of Calif.; Craig E. Mixan, Midland, Mich.

[73] Assignee: The Dow Chemical Company, Midland, Mich.

[21] Appl. No.: 711,543

[22] Filed: Mar. 13, 1985

Related U.S. Application Data

[60] Continuation of Ser. No. 467,710, Feb. 25, 1983, abandoned, which is a continuation-in-part of Ser. No. 343,055, Jan. 27, 1982, which is a division of Ser. No. 243,166, Mar. 12, 1981, Pat. No. 4,331,811.

[51] Int. Cl.$^4$ ............................................. C07D 213/26
[52] U.S. Cl. ..................................... 546/345; 546/346
[58] Field of Search ................................ 546/345, 346

[56] References Cited

U.S. PATENT DOCUMENTS 4,256,894  3/1981  Dietsche et al. ..................... 546/345

Primary Examiner—Alan L. Rotman
Attorney, Agent, or Firm—Merlin B. Davey

[57] ABSTRACT

Preparation of 2,3-dichloro-5-trichloromethylpyridine in high yields and purity by chlorinating 2-chloro-5-trichloromethylpyridine at 70° to 250° C. with chlorine in the presence of a catalyst containing one or more molybdenum, tungsten or ruthenium compounds.

6 Claims, No Drawings

PREPARATION OF 2,3-DICHLORO-5-TRICHLOROMETHYLPYRIDINE

CROSS-REFERENCE TO RELATED APPLICATION

This application is a Rule 60 continuation of application Ser. No. 467,710 filed Feb. 25, 1983, now abandoned which is a continuation-in-part of application Ser. No. 343,055 filed Jan. 27, 1982 abandoned which is a divisional of application Ser. No. 243,166 filed Mar. 12, 1981 U.S. Pat. No. 4,331,811.

BACKGROUND OF THE INVENTION

Chlorinated pyridine derivatives are known compounds and have been prepared by a number of processes. Such processes include, for example, those described in U.S. Pat. Nos. 3,420,833; 3,244,722; 3,732,230; 3,186,994; 3,538,100; British Pat. No. 957,276 and copending application No. 16,646 filed Mar. 1, 1979. The products of these processes have been used as herbicides and pesticides and as chemical intermediates in the preparation of other highly desired herbicide or pesticide products. Of the many chlorinated pyridine derivatives, 2,3-dichloro-5-trichloromethylpyridine is a particularly desirable intermediate for the preparation of selective herbicides having wide utility in the presence of valuable crops.

SUMMARY OF THE INVENTION

In accordance with this invention, 2,3-dichloro-5-trichloromethylpyridine is prepared in high yields and high purity by a process which comprises contacting 2-chloro-5-trichloromethylpyridine in the liquid state with chlorine in the presence of a catalyst at a temperature of 70° to 250° C., the improvement comprising employing an effective amount of a catalyst selected from the group consisting of tungsten hexachloride, molybdenum pentachloride, tungsten oxytetrachloride, molybdenum oxytetrachloride and ruthenium chloride. The preferred catalysts are those containing tungsten or molybdenum.

The resulting 2,3-dichloro-5-trichloromethylpyridine may be separated from the reaction mixture or the reaction mixture may be used as is, with or without removing any catalyst residues, in a fluorination reaction to prepare, for example, 2,3-dichloro-5-trifluoromethylpyridine.

The starting 2-chloro-5-trichloromethylpyridine is contacted in the liquid state with chlorine at temperatures of 70° to 250° C., preferably 150° to 200° C., and at atmospheric or superatmospheric pressures of up to about 200 psig or more, in the presence of an effective amount, advantageously about 0.01 to about 10 weight percent, preferably about 0.5 to about 5 weight percent, of the catalyst.

The process of the present invention is preferably conducted under essentially anhydrous conditions, and is preferably carried out in a continuous, cyclical operation, although batch operations may be employed, if desired.

DETAILED DESCRIPTION OF THE INVENTION

In carrying out the process of the present invention, gaseous chlorine is passed into the liquid 2-chloro-5-trichloromethylpyridine starting material at a temperature of at least 70° C., in the presence of the desired catalyst. At least an equimolar amount of the chlorine gas reactant is employed with from 0.3 to about 10 excess molar proportions of chlorine per mole of starting material desirably being employed. The continuous passage of excess chlorine gas through the reaction mixture serves not only to supply a large amount of reactant but to sweep out any carbon tetrachloride or hydrogen chloride by-products. The most suitable rate at which the chlorine gas is fed will vary with the reaction temperature, pressure, reaction mixture volume, etc. An excess amount of from about 0.3 to about 5.0 moles of chlorine per hour is usually employed per mole of 2-chloro-5-trichloromethylpyridine.

The degree of catalytic activity may vary depending on the reaction conditions. However, those skilled in the art can, by routine experimentation, readily determine the optimum catalyst and amount thereof required for any particular set of pressure, temperature or time conditions desired. Catalysts bonded to an inert support such as, for example, alumina, silica, silica alumina, various clays and molecular sieves are also contemplated for use in the present invention.

Generally, an increase of 10° to 15° C. in the temperature range has the effect of approximately doubling the reaction rate. The reaction rate also increases with increased catalyst concentration.

The 2-chloro-5-trichloromethylpyridine is known and can be prepared according to the methods described in the known art.

The following examples further illustrate the present invention but are not to be construed as limiting. Unless otherwise indicated, all parts and percentages are by weight.

EXAMPLE 1

A mixture of 23.1 g (0.1 mole) of 2-chloro-5-trichloromethylpyridine and 2.0 g (0.005 mole) of tungsten hexachloride ($WCl_6$) was heated at 120° C. while sparging in chlorine for 42.5 hours. Vapor phase chromatography (VPC) indicated 18 percent 2,3-dichloro-5-trichloromethylpyridine. The reaction mixture was then heated to 170° to 175° C. for an additional 7 hours with the addition of chlorine and was then found (VPC) to contain about 95 percent 2,3-dichloro-5-trichloromethylpyridine.

The reaction mixture was diluted with hexane and washed with water. The organic layer was separated, dried with $MgSO_4$ and the solvent removed by evaporation to give 26.7 g of yellow liquid. Distillation gave 24.9 g of 95.6 percent 2,3-dichloro-5-trichloromethylpyridine (89.7 percent yield). The impurities were analyzed and found to be:

2,3,5,6-tetrachloropyridine (1.6%)
2-chloro-5-trichloromethylpyridine (1.6%)
2,3,6-trichloro-5-trichloromethylpyridine (1.2%)

EXAMPLE 2

Chlorine was slowly sparged into a mixture of 5773 g (25 moles) of 2-chloro-5-trichloromethylpyridine and 496 g (1.25 moles, 5 mol percent) of tungsten hexachloride which was heated to 175° to 185° C. After 27.5 hours, the reaction mixture was cooled and dissolved in carbon tetrachloride. The organics were washed with a sodium carbonate solution and dried over anhydrous sodium carbonate. Evaporation of the solvent gave 6793 g of a yellow orange liquid. Analysis of the product by gas chromatography indicated 94.2 percent 2,3-dichloro-5-trichloromethylpyridine.

EXAMPLE 3

The experiment of Example 1 was repeated using 1.37 g (0.005 mole) of molybdenum pentachloride as catalyst and a temperature of 170° to 175° C. After 13.5 hours, the product was worked up and dried as in Example 1. Distillation through a Vigreux column afforded 23.5 g of a colorless liquid which was 94.5 percent 2,3-dichloro-5-trichloromethylpyridine. The impurities were analyzed and found to be:
2,3,5,6-tetrachloropyridine (1.7%)
2-chloro-5-trichloromethylpyridine (2.7%)
2,3,6-trichloro-5-trichloromethylpyridine (1.1%)

EXAMPLE 4

Example 3 was repeated using 25 g (0.11 mole) of 2-chloro-5-trichloromethylpyridine and 1.25 g (5 weight percent) of molybdenum pentachloride as the catalyst. After 8.5 hours of reaction the product was worked up as in Example 2. Obtained 20.5 g of yellow liquid having the following composition (gas chromatography):
2,3-dichloro-5-trichloromethylpyridine (95.3%)
2-chloro-5-trichloromethylpyridine (1.9%)
2,3,6-trichloro-5-trichloromethypyridine (2.0%)

EXAMPLE 5

Chlorine was slowly sparged into a mixture of 23 g (0.1 mole) of 2-chloro-5-trichloromethylpyridine and 2.5 g (10 weight percent) of molybdenum oxytetrachloride (MoCl$_4$O) and heated to 170° C. for 12 hours. The mixture of reaction products was found (gas chromatography) to have the following composition:
2,3-dichloro-5-trichloromethylpyridine (76.5%)
2-chloro-5-trichloromethylpyridine (2.0%)
2,3,6-trichloro-5-trichloromethylpyridine (1.8%)
2,3,5,6-tetrachloropyridine (11.8%)
pentachloropyridine (3.9%)
2,3,6-trichloropyridine (3.2%)

EXAMPLE 6

Chlorine was slowly sparged into a mixture of 2-chloro-5-trichloromethylpyridine (23.1 g, 0.1 mole) and ruthenium chloride (1.04 g, 0.005 mole) at 175° to 180° C. for 29.5 hours. After the reaction mixture cooled, it was diluted with toluene and the ruthenium salts which precipitated were removed by filtration. The organic layer was washed with a saturated solution of sodium chloride and dried with MgSO$_4$. Removal of the drying agent and solvent afforded a light brown liquid which upon analysis by gas chromatography was found to contain the following:
2,3-dichloro-5-trichloromethylpyridine (73%)
2-chloro-5-trichloromethylpyridine (10%)
2,3,6-trichloro-5-trichloromethylpyridine (14)
2,6-dichloro-3-trichloromethylpyridine (2%)

EXAMPLE 7

Mixtures of 1000 g of 2-chloro-5-trichloromethylpyridine and varying amounts of tungsten hexachloride were individually placed in 2-liter, high pressure, monel stirred reactors and 30 g/hr of chlorine were bubbled through the mixtures at 175° C. at the pressures indicated in the following table. The amounts of catalyst, times and results are shown in the table.

| Run | Pressure, psig | Mole % WCl$_6$ | Hours | Product, Wt. Percent | | | |
|---|---|---|---|---|---|---|---|
| | | | | A | B | C | D |
| 1 | 100 | 3 | 20 | 1.1 | 80.8 | 11.4 | 0.5 |
| 2 | 50 | 3 | 24 | 0.9 | 78.6 | 11.0 | 0.5 |
| 3 | 50 | 2 | 28 | 0.7 | 86.7 | 7.7 | 0.5 |
| 4 | 50 | 0.5 | 45 | 3.1 | 81.3 | 12.7 | 0.9 |
| 5 | 100 | 0.5 | 48 | 0.5 | 78.8 | 14.3 | 1.2 |

A = 2-chloro-5-trichloromethylpyridine (2-Tet)
B = 2,3-dichloro-5-trichloromethylpyridine (2,3-Penta)
C = 2,3,6-trichloro-5-trichloromethylpyridine (2,3,6-Hex)
D = 2,3,4,6-tetrachloropyridine
Product analysis was by internal standard gas chromatography.

EXAMPLE 8

Mixtures of 194 g of 2-chloro-5-trichloromethylpyridine and varying amounts of tungsten hexachloride were individually placed in 250 ml round bottom flasks and 4.8 g/hr of chlorine were bubbled through at atmospheric pressure and various temperatures. The product was analyzed by internal standard gas chromatography. The results are given in the following table.

| Run | Pressure, psig | Mole % WCl$_6$ | Hours | Product, Wt. Percent | | | |
|---|---|---|---|---|---|---|---|
| | | | | A | B | C | D |
| 1 | 170 | 0.5 | 115 | 2.9 | 87.3 | 6.0 | 0.4 |
| 2 | 175 | 2 | 24 | 1.9 | 86.0 | 4.3 | 0.6 |
| 3 | 180 | 0.5 | 96 | 0.6 | 85.6 | 10.1 | 0.7 |
| 4 | 175 | 0.5 | 122 | 0.5 | 87.7 | 8.4 | 0.4 |
| 5 | 175 | 0.25 | 141 | 2.6 | 76.8 | 10.6 | 0.6 |

Note:
A, B, C and D are the same products as in Example 7.

EXAMPLE 9

In a 100 gallon Pfaudler, 697 lbs of 98.4% 2-Chloro-5-trichloromethylpyridine and 36.5 lbs of WCl$_6$ were reacted with 10 lbs/hr Cl$_2$ for 54.5 hours at 175° C. and atmospheric pressure. The catalyst was removed by adding first 522 lbs CCl$_4$ and then 103 lbs Na$_2$CO$_3$ in 598 lbs H$_2$O to the reaction mixture (in two batches). The aqueous layer, containing the tungsten as sodium tungstate, was removed and the CCl$_4$ was stripped away from the organic layer to give 777 lbs of crude product containing 86% 2,3-Penta, 5% 2,3,6-Hex and 5.5% CCl$_4$. Two hundred twenty grams of this mixture and 9.5 g of FeCl$_3$ were fluorinated in the laboratory in a 1 liter covered Teflon ® beaker. HF was bubbled into the mixture at atmospheric pressure and 175° C. for 14 hours. One hundred sixty-five grams of product were recovered which contained 58 area percent 2,3-dichloro-5-trifluoromethylpyridine (CF$_3$), 24.4 area percent 2,3-dichloro-5-chlorodifluoromethylpyridine (CF$_2$Cl), 7.4 area percent 2,3-dichloro-5-fluorodichloromethylpyridine (CFCl$_2$), and 10 area percent 2-fluoro-3-chloro-5-trifluoromethylpyridine.

EXAMPLE 10

In a stirred, 250 ml round bottom flask, 193.5 g of 92.1% 2-Tet and 1.67 g WCl$_6$ were chlorinated for 122 hours at 175° C., atmospheric pressure, and a Cl$_2$ flow-rate of 4.8 g/hr. This material, which contained 87.7% 2,3-Penta and 8.44% 2,3,6-Hex, was then transferred directly to a 1 liter, covered Teflon ® beaker and 6.11 g of FeCl$_3$ were added. HF was bubbled into the mixture of 175° C. and atmospheric pressure for 39.5 hours, at which point the reaction mixture contained 63 area percent CF$_3$, 4.4 area percent CF$_2$Cl and 22.7 area percent ring fluorination. HCl was then added to reverse the ring fluorination to give 80.0 area percent $CF_3$ and 6.9 area percent ring fluorination.

EXAMPLE 11

In a 300 gallon Pfaudler, 2750 lbs of 97.7% 2-Tet and 48.1 lbs of $WCl_6$ were reacted with 16 lbs/hr $Cl_2$ for 113 hours at 175° C. and 20 psig. The crude product was washed with an aqueous sodium carbonate solution to remove the $WCl_6$ as in Example 9. The product (1,230 lbs), which contained 77.5% 2,3-Penta, 12.5% 2,3,6-Hex and approximately 9% $CCl_4$ was transferred to a 150 gallon nickel reactor. $FeCl_3$ (38.5 lbs) was added and the mixture was reacted with 4 lbs/hr HF at 170° C. and 15 psig. After 94 hours, the HF feed was stopped and 3 lbs/hr HCl were added for 40 hours to reverse the ring fluorination. The final product was 986 lbs containing 64.0% $CF_3$ and 36% others.

EXAMPLE 12

In a 300 gallon Pfaudler, 2711 lbs of 96.8% 2-Tet and 23.5 lbs of $WCl_6$ were reacted with 7.8 lbs/hr $Cl_2$ for 158 hours at 175° C. The pressure was 50 psig for the first 42 hours and 20 psig from then on. The product (1,219 lbs) from this reaction (no catalyst removal was done), which contained 75.0% 2,3-Penta and 19.9% 2,3,6-Hex, was transferred to a 150 gallon nickel reactor. $FeCl_3$ (37.4 lbs) was added and the mixture was reacted with 5 lbs/hr HF at 170° C. and 15 psig. After 51.5 hours the HF feed was stopped and 3 lbs/hr HCl were added for 9 hours. The final product was 853 lbs containing 35.8% $CF_3$, 26.1% $CF_2Cl$, 5.2% $CFCl_2$, 13.2% 2,3,6-trichloro-5-chlorodifluoromethylpyridine and 6.8% 2,3,6-trichloro-5-trifluoromethylpyridine.

Various modifications may be made in this invention without departing from the spirit or scope thereof and it is understood that we limit ourselves only as defined in the appended claims.

What is claimed is:

1. In a process for preparing 2,3-dichloro-5-trichloromethylpyridine by contacting 2-chloro-5-trichloromethylpyridine in the liquid state with chlorine in the presence of a catalyst at a temperature of 70° to 250° C., and at a pressure of from atmospheric pressure to 200 psig, the improvement comprising employing an effective amount of a catalyst selected from the group consisting of tungsten hexachloride, molybdenum pentachloride, tungsten oxytetrachloride, molybdenum oxytetrachloride and ruthenium chloride, whereby 2,3-dichloro-5-trichloromethylpyridine is obtained in a yield of at least 70 percent of final product.

2. Process of claim 1 wherein the temperature is from 150° to 200° C.

3. Process of claim 1 wherein the reaction is carried out under ambient pressure conditions.

4. Process of claim 1 wherein the reaction is carried out under elevated pressure conditions.

5. Process of claim 1 wherein the catalyst is tungsten hexachloride.

6. Process of claim 1 wherein the catalyst is molybdenum pentachloride.

* * * * *